United States Patent
Olah et al.

(10) Patent No.: US 8,461,218 B2
(45) Date of Patent: *Jun. 11, 2013

(54) RENDERING PETROLEUM OIL AS AN ENVIRONMENTALLY CARBON DIOXIDE NEUTRAL SOURCE MATERIAL FOR FUELS, DERIVED PRODUCTS AND AS A REGENERATIVE CARBON SOURCE

(75) Inventors: George A. Olah, Beverly Hills, CA (US); G. K. Surya Prakash, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 542 days.

This patent is subject to a terminal disclaimer.

(21) Appl. No.: 12/755,975

(22) Filed: Apr. 7, 2010

(65) Prior Publication Data

US 2010/0261937 A1   Oct. 14, 2010

Related U.S. Application Data

(60) Provisional application No. 61/168,307, filed on Apr. 10, 2009.

(51) Int. Cl.
*C07C 27/00* (2006.01)

(52) U.S. Cl.
USPC ............................ 518/703; 518/700; 518/704

(58) Field of Classification Search
USPC .......................................... 518/700, 703, 704
See application file for complete search history.

(56) References Cited

U.S. PATENT DOCUMENTS

| | | | |
|---|---|---|---|
| 7,378,561 B2 | 5/2008 | Olah et al. | 568/885 |
| 2006/0235088 A1 | 10/2006 | Olah et al. | 518/702 |
| 2007/0244208 A1* | 10/2007 | Shulenberger et al. | 518/726 |
| 2007/0254969 A1 | 11/2007 | Olah et al. | 518/726 |
| 2008/0293976 A1 | 11/2008 | Olah et al. | 568/698 |
| 2008/0319093 A1 | 12/2008 | Olah et al. | 518/700 |

FOREIGN PATENT DOCUMENTS

| WO | WO 2008/021700 A1 | 2/2008 |
|---|---|---|
| WO | WO 2008/157673 A1 | 12/2008 |

OTHER PUBLICATIONS

International Search Report and Written Opinion of the International Searching Authority, application No. PCT/US2010/030245, Aug. 17, 2010.

* cited by examiner

*Primary Examiner* — Jafar Parsa
(74) *Attorney, Agent, or Firm* — Winston & Strawn LLP

(57) ABSTRACT

The invention provides a method for rendering petroleum oil as an essentially environmentally carbon dioxide-neutral fuel and source material. Carbon dioxide produced from petroleum oil combustion is captured, purified, combined with steam and light hydrocarbon fractions, or with hydrogen, and reacted under reaction conditions sufficient to form methanol and/or dimethyl ether, which can be used as fuel or feedstock for derived synthetic hydrocarbons and products.

22 Claims, No Drawings

RENDERING PETROLEUM OIL AS AN ENVIRONMENTALLY CARBON DIOXIDE NEUTRAL SOURCE MATERIAL FOR FUELS, DERIVED PRODUCTS AND AS A REGENERATIVE CARBON SOURCE

CROSS REFERENCE TO RELATED APPLICATIONS

This application claims the benefit of U.S. application No. 61/168,307 filed Apr. 10, 2009, the entire content of which is incorporated herein by reference thereto.

BACKGROUND

Energy and fuels are essential in modern life. Most widely used type of fuels are fossil fuels. Fossil fuels, including petroleum oil, are essentially hydrocarbons containing carbon and hydrogen in various ratios.

Petroleum oil, like any carbon-containing fuel, forms carbon dioxide upon its combustion, and therefore is not renewable on the human timescale. Also, because carbon dioxide is a greenhouse gas, combustion of oil contributes to global warming. It has been suggested to mitigate harmful carbon dioxide emissions by imposing carbon quota or by capturing carbon dioxide emissions and sequestering it underground or at the bottom of the sea. Sequestration, however, is a costly and only a temporary solution that presents a risk that sequestered carbon dioxide may be released with deadly catastrophic consequences in geological events such as earthquakes and slides.

Thus, it would be desirable to make petroleum oil use environment-friendly by effectively addressing its carbon dioxide emission and at the same time render it a regenerative carbon source.

SUMMARY OF THE INVENTION

The present invention provides a method for rendering petroleum oil as an essentially environmentally carbon dioxide-neutral fuel and regenerative carbon source for producing methanol or dimethyl ether and their derived products, by chemically recycling carbon dioxide formed upon petroleum oil refining or combustion.

In an embodiment, the method comprises: subjecting petroleum oil to conditions of refining or combustion sufficient to produce carbon dioxide; capturing and purifying the produced carbon dioxide; combining the carbon dioxide with water and a suitable light hydrocarbon fraction, preferably saturated hydrocarbons (methane, ethane, propane and butanes), or with hydrogen under reaction conditions sufficient to produce methanol or dimethyl ether, so that the carbon dioxide produced from the petroleum oil is not emitted to the atmosphere, thus rendering the petroleum oil as a carbon dioxide-neutral fuel.

The method can further comprise utilizing the methanol so produced from carbon dioxide for use as a fuel or feedstock; subjecting the methanol or derived dimethyl ether fuels or products made from the feedstock to reaction conditions to generate carbon dioxide; and repeating the capturing, combining, recycling and subjecting steps on the generated carbon dioxide so that the carbon dioxide produced from the methanol fuel or products made from the methanol feedstock also is not adversely emitted to the atmosphere.

In an example, the carbon dioxide, methane/natural gas, and water are combined in a molar ratio of about 3:2:1 and are reacted in separate steps or in a single step to produce methanol.

In an embodiment, carbon dioxide is electrochemically reduced to formic acid and related intermediates, which subsequently can be converted to methanol through methyl formate intermediate, as disclosed in U.S. Pat. Application Publication Nos. 2006/0235088 and 2007/0254969.

In an embodiment, the method comprises: refining or combusting petroleum oil to produce carbon dioxide; capturing the produced carbon dioxide on an adsorbent; and treating the adsorbent to release the captured carbon dioxide therefrom for use in producing methanol or dimethyl ether. The adsorbent is treated with, for example, sufficient heating, reduced pressure, vacuum, gas purge, or a combination thereof to release the captured carbon dioxide. The absorbent can be any known material suitable for capturing carbon dioxide. Preferably, the adsorbent comprises a polyamino-containing polymer, such as polyethyleneimine, deposited on a nanostructured support having a high surface area, e.g., nanostructured fused silica or alumina described in U.S. Pat. Application Publication No. 2008/0293976.

In an embodiment, the method further comprises reacting the carbon dioxide with a suitable light hydrocarbon fraction and steam under steam reforming reaction conditions sufficient to form a mixture of hydrogen and carbon monoxide and reacting the carbon dioxide with a suitable hydrocarbon fraction under dry reforming reaction conditions sufficient to form another mixture of hydrogen and carbon monoxide. The hydrogen and carbon monoxide produced in the steam and dry reforming are then combined for an overall bi-reforming process to form a mixture of hydrogen and carbon monoxide in a molar ratio of about 2 moles of hydrogen to 1 mole of carbon monoxide for reaction to form methanol or dimethyl ether. The molar ratio of hydrogen to carbon monoxide mixture is at least 2:1, and preferably between 2:1 and 2.1:1.

The steam reforming and the dry reforming can be performed simultaneously in a single bireforming step. In an example, bireforming is performed over a catalyst at a temperature between about 800° C. and 1100° C. Suitable catalysts include a single metal catalyst, a single metal oxide catalyst, a mixed catalyst of a metal and a metal oxide, or a mixed catalyst of at least one metal oxide and another metal oxide. The catalyst can be provided on an oxide support. In an example, the catalyst comprises V, Ti, Ga, Mg, Cu, Ni, Mo, Bi, Fe, Mn, Co, Nb, Zr, La or Sn, or an oxide thereof. For example, the catalyst can be NiO or a mixed catalyst of NiO, $V_2O_5:Ni_2O_3$, $Ni_2V_2O_7$ and $Ni_3V_2O_5$. The catalyst can be provided on a support of a high surface area nano-structured fumed alumina or fumed silica. In an example, the catalyst is NiO supported on fumed alumina or $NiO/V_2O_5$ supported on fumed silica.

Suitable hydrocarbon sources used in the present processes, which preferably are methane, natural gas, or light oil fractions, can be obtained from any available source, including coalbed methane accompanying coal mining or any other natural source.

Hydrogen needed for the chemical recycling of carbon dioxide according to the present processes can be directly generated from water, e.g., by electrolysis or any other means of cleavage, or by photochemical or thermal decomposition, using any energy source, including electricity generated by fossil fuel-burning power plants, e.g., during off-peak periods, or any alternate energy source (e.g., solar, wind, hydro or atomic energy).

In an example, methanol produced according to the invention is dehydrated by removing water under conditions sufficient to produce dimethyl ether, and the removed water is reused during reforming, such as in the bi-reforming process.

The methanol produced according to the present process can be used as is or can be converted to dimethyl ether. Methanol and dimethyl ether can then be used as fuel or chemical feedstock for the production of various derived products. Thereafter, the methanol fuel or products made from the feedstock can be subjected to reaction conditions to generate carbon dioxide and the capturing, combining, recycling and subjecting steps are repeated on the generated carbon dioxide so that the carbon dioxide produced from the methanol fuel or products made from is also not emitted to the atmosphere.

Dimethyl ether produced according to the present processes can be reacted in the presence of an acidic-basic or zeolitic catalyst under conditions sufficient to form ethylene or propylene. Ethylene or propylene can in turn be converted to produce synthetic hydrocarbons, chemicals, polymers, or various products derived therefrom.

The synthetic hydrocarbons, chemicals, and polymers can be subjected to use or further treatment, which results in combustion to generate carbon dioxide. Also, the produced methanol can be combusted as a fuel to produce energy and generating carbon dioxide with the generated carbon dioxide recycled to the other process steps for producing methanol. This avoids release of the carbon dioxide into the atmosphere and avoids having to otherwise handle or sequester carbon dioxide.

The method can be carried out while co-generating electricity or energy from petroleum oil combustion. For example, the method can be carried out in an electricity-producing oil-burning power plant. Methanol produced according to the present method can be combusted, optionally in a mixture that includes gasoline, in a power plant that produces energy with the combusted methanol. Carbon dioxide generated from combusting methanol is recycled for producing methanol. Similarly, dimethyl ether produced according to the present method can be combusted, optionally in a mixture that includes natural gas, in a power plant that produces energy while also generating carbon dioxide. The carbon dioxide so generated is recycled for producing methanol, which can be used to produce additional dimethyl ether.

Thus, the present processes advantageously provide the recycling of carbon dioxide from refining or combustion of petroleum oil for the production of methanol, dimethyl ether, and their derived products in an integrated, efficient and economical industrial operation that is environmentally beneficial by not releasing the carbon dioxide into the atmosphere.

DESCRIPTION OF THE PREFERRED EMBODIMENTS

The invention relates to processes for the capture, isolation and purification of carbon dioxide from petroleum oil combustion and its chemical recycling to methanol and dimethyl ether.

A preferred embodiment of the invention relates to a method for rendering petroleum oil as an essentially environmentally carbon dioxide-neutral fuel and regenerative carbon source for producing methanol or dimethyl ether, by subjecting petroleum oil to refining or combustion conditions sufficient to produce carbon dioxide; capturing and purifying the produced carbon dioxide; and combining the purified carbon dioxide with water and a suitable light hydrocarbon fraction or with hydrogen produced from water under reaction conditions sufficient to produce methanol or dimethyl ether, so that the carbon dioxide generated from the petroleum oil is not introduced into the atmosphere, thus rendering the petroleum oil as an essentially environmentally carbon dioxide-neutral fuel and regenerative carbon source.

By chemically recycling carbon dioxide formed from oil use to produce methanol and/or dimethyl ether, the invention advantageously renders petroleum oil a regenerative carbon source for producing methanol and dimethyl ether. And if the methanol or dimethyl ether is combusted to generate carbon dioxide and the carbon dioxide is subsequently recovered and recycled for making more methanol or dimethyl ether, those compounds will also become environmentally neutral with the carbon dioxide not released into the atmosphere and instead being continuously chemically recycled to produce methanol and dimethyl ether.

The invention thus advantageously renders petroleum oil essentially environmentally carbon dioxide-neutral fuel. As used herein, "environmentally carbon dioxide-neutral fuel" means that the petroleum oil fuel is used in such a way that its use does not release or introduce carbon dioxide into the environment, i.e., carbon dioxide is not released into the atmosphere or is sequestered. Thus, the present processes of rendering petroleum oil as an essentially environmentally carbon dioxide-neutral fuel reduces the carbon footprint of using petroleum oil and are environmentally beneficial. As used herein, "essentially environmentally carbon dioxide-neutral fuel" and "substantially environmentally carbon dioxide-neutral fuel" mean that petroleum oil is used in such a way (i.e. refined or combusted) that its use does not release or introduce carbon dioxide into the environment except in minor amounts, e.g., less than 10%, preferably less than 5%, and more preferably less then 3%, of the total carbon dioxide produced from using the petroleum oil.

In an embodiment, carbon dioxide is captured following petroleum oil refining or combustion, purified and chemically recycled by reaction into methanol, which can be used as a fuel or chemical feedstock. Methanol can be converted to dimethyl ether, which can be utilized as a fuel for transportation or as household gas for heating and cooking. Methanol and dimethyl ether can be converted into ethylene or propylene, which can be used as building blocks of synthetic hydrocarbons, chemicals, and polymers, which in turn can be used to produce various products.

The present processes can be used with any method of oil refining or combustion as well as any method of generating energy from oil that produces carbon dioxide. For example, the processes can be used to recycle carbon dioxide formed from any oil refining process or from oil combustion in power plants and industrial plants. Recycled methanol produced according to the present processes can be combusted as a transportation fuel, optionally in a mixture that includes gasoline (flexfuel) or in any power plant that produces energy with the combusted methanol, thus also generating carbon dioxide.

Carbon dioxide produced by the refining or combustion of petroleum oil is captured, isolated and purified using suitable, known methods, e.g., by membrane separation or with a suitable absorbing device or material. A suitable process for capturing and reversibly adsorbing carbon dioxide from a gas mixture by using a nano-structured supported absorbent such as fumed silica is disclosed in U.S. Pat. No. 7,378,561, the entire content of which is incorporated herein by reference. Captured carbon dioxide can be readily released through, for example, heating, reduced pressure, vacuum, gas purge, or a combination thereof, for use in the reactions described herein. Prior to its utilization, carbon dioxide is purified by any suitable, known method, e.g., by absorbing pollutants and contaminants therein. The captured and/or purified carbon dioxide is then recycled and converted to methanol or dimethyl ether.

A light hydrocarbon fraction of oil refining (containing $C_1$ to $C_4$ alkanes preferentially) and carbon dioxide is converted to methanol and/or dimethyl ether using a process of conversion that is referred to as bi-reforming (described in U.S. Pat. Application Publication No. 2008/0319093) and that utilizes a specific combination of steam ($H_2O$) reforming and dry ($CO_2$) reforming of methane, performed in two steps or combined into a single step. The method comprises reacting methane ($C_1$ alkane) and higher homologues under a combination of conditions of steam (wet) and dry ($CO_2$) reforming in a specific molar ratio of reactants sufficient to produce a mixture of hydrogen and carbon monoxide ($H_2$/CO) in a molar ratio of about 2:1, which is sufficient to convert such mixture of $H_2$ and CO exclusively to methanol or dimethyl ether. In a preferred embodiment, the molar ratio of hydrogen and carbon monoxide is between 2:1 and 2.1:1. Advantageously, the mixture of reactants is treated without separation of its components to convert substantially all the reactants to methyl alcohol or dimethyl ether without producing byproducts.

The individual steps of the process of the invention for the formation of methanol are illustrated by the following reactions:

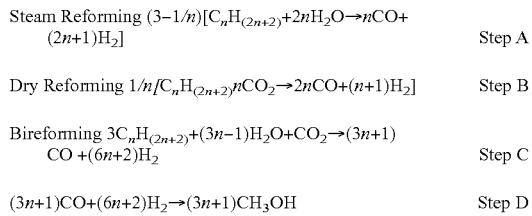

| | |
|---|---|
| Steam Reforming $(3-1/n)[C_nH_{(2n+2)}+2nH_2O \rightarrow nCO+(2n+1)H_2]$ | Step A |
| Dry Reforming $1/n[C_nH_{(2n+2)}nCO_2 \rightarrow 2nCO+(n+1)H_2]$ | Step B |
| Bireforming $3C_nH_{(2n+2)}+(3n-1)H_2O+CO_2 \rightarrow (3n+1)CO+(6n+2)H_2$ | Step C |
| $(3n+1)CO+(6n+2)H_2 \rightarrow (3n+1)CH_3OH$ | Step D |

The process of producing methanol can be practiced by carrying out the reforming steps separately. The products of reforming of steps A and B are mixed to provide close to 2:1 ratio of $H_2$ and CO before being introduced into the methanol producing step. The two reforming steps can also be combined into a single step C (bi-reforming) following the shown substrate ratios to obtain a mixture of hydrogen and carbon monoxide in approximately 2:1 ratio for subsequent methanol conversion (Step D).

The above process completely recycles carbon dioxide to methanol without producing any byproduct, such that no carbon dioxide is released into the atmosphere or needs to be sequestered. This provides significant economical and environmental advantages. For example, in contrast to the known tri-reforming process of natural gas, in which a combination of dry reforming, steam reforming and partial oxidation of methane is carried out in a single step but which produces $CO_2$ as a significant excess byproduct in the oxidation step, the present process provides improved control, high selectivity, and high yield of the conversion of carbon dioxide to methanol, without producing any byproducts and the disadvantages associated with concurrent partial oxidation that results in undesirable excess carbon dioxide.

When producing dimethyl ether, water obtained from the dehydration of methanol can be recycled in the bi-reforming of carbon dioxide with alkanes. This is particularly advantageous in arid areas or places where pure water is not readily available.

$(3n+1)CH_3OH \rightarrow (3n+1)/2CH_3OCH_3+(3n+1)/2H_2O$

In the case of methane, in particular, water formed during dehydration can be totally recycled.

$3CH_4+CO_2 \rightarrow 2CH_3OCH_3$ (overall)

Dehydration of the methanol can be effected over a suitable silica alumina, or other solid acidic catalyst, including polymeric sulfonic acid catalysts such as Nafion-H, at a temperature sufficient for the removal of the water. Operative temperature are in the range of 100° C. to 200° C.

The bi-reforming process for recycling of $CO_2$ using methane produces a $H_2$/CO mixture with a molar ratio of at least 2 to 1 required for methanol synthesis. In the subsequent methanol synthesis step, substantially all of the hydrogen is converted to methanol. As described in U.S. Pat. Application Publication Nos. 2006/0235088 and 2007/0254969, this subsequent step can be performed, without limitation, by direct catalytic conversion, or by a reaction that involves methyl formate intermediate.

In a preferred embodiment of this invention, a specific combination of steam and dry reforming of methane is used to achieve a molar ratio of $H_2$ and CO close to at least 2 moles hydrogen to 1 mole of carbon monoxide for the conversion to methanol. The single step bireforming conversion temperature is in the range from about 800° C. to about 1100° C., preferably about 850° C. to about 950° C. A catalyst or a combination of catalysts can be used. Suitable catalysts include alkali oxides, alkaline oxides or metal oxides, such as V, Ti, Ga, Mg, Cu, Mo, Bi, Fe, Mn, Co, Nb, Zr, La or Sn. Catalysts can be used alone in combination, and can be supported on a suitable high surface area support such as silica or alumina. Exemplary single or metal oxide combinations include NiO, NiO:$V_2O_5$, $V_2O_5$:$Ni_2O_3$, metal-metal oxides such as $N_1$—$V_2O_5$, ($M_2O_3$—$V_2O_5$), and mixed oxides such as $Ni_2V_2O_7$, $Ni_3V_2O_5$ and $Ni_3V_2O_8$. In a preferred embodiment, the catalyst is NiO supported on fumed alumina or NiO/$V_2O_5$ supported on fumed silica. It will be appreciated that a number of other related metal and metal oxide catalysts, and their combinations, can be used. Suitable reactors for the conversion reactions can be used. For example, a continuous flow reactor under appropriate reaction conditions can be used.

The energy required for the present processes for chemical recycling of carbon dioxide can be provided from any suitable source. For example, when practicing the process in an oil burning power plant, the energy produced by the power plant itself in off peak usage periods can be used. In other examples, any alternative energy (solar, wind, water (hydro), etc.) or atomic energy sources can be used. The present recycling process of carbon dioxide from oil refining or combustion to produce methanol and/or dimethyl ether is an efficient energy storage and fuel production process that can use any available energy to produce useful products and eliminate carbon dioxide emissions.

In the absence of a convenient and economical hydrocarbon source, the processes can directly utilize hydrogen. Hydrogen needed for the reduction of carbon dioxide can be obtained by known methods of electrolysis or cleavage of water. Energy for this purpose can be provided from any of the previously mentioned energy sources or by photolytic, thermal or enzymatic ways. The utilization of water as the needed hydrogen source for the conversion of recycled carbon dioxide is described in U.S. Pat. Application Publication No. 2007/0254969.

In an embodiment, efficient and economical aqueous electrochemical conversion of $CO_2$ to methanol is provided. $CO_2$ can be electrochemically reduced with good selectivity to formic acid, as described in U.S. Pat. Application Publication No. 2007/0254969:

$CO_2+2H^++2e^- \rightarrow HCOOH$

Formic acid is then combined with methanol (to be recycled from the process) to form methyl formate, which is subsequently hydrogenated to form exclusively two moles of methanol under relatively mild conditions:

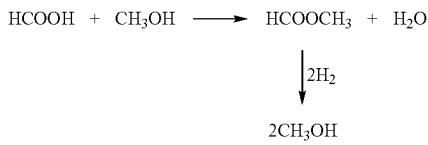

This embodiment allows significant energy savings, since hydrogen is used only in producing methanol, and the needed hydrogen can come from formic acid itself.

Advantageously, the present processes achieve substantially complete recycling of carbon dioxide to produce methanol and/or dimethyl ether, thus providing an efficient and economical way of rendering petroleum oil a regenerative, environmentally carbon dioxide-neutral fuel and chemical source.

In the present processes, carbon dioxide formed upon oil combustion is captured and chemically recycled to methanol and/or dimethyl ether. This makes possible efficient and economical cogeneration of electricity and production of methanol and dimethyl ether (as well as various products derived therefrom) in an integrated industrial cycle of substantial utility and value. The present processes also allow efficient load management of oil-burning power plants during off-peak periods.

Methanol and dimethyl ether produced according to the invention can be used in numerous applications, either by themselves or upon subsequent conversion to other products. For example, methanol, dimethyl ether and their derived products can be used as synthetic internal combustion (ICE) fuels, gasoline-methanol mixed fuels (prepared by adding methanol to gasoline with the fuel having a minimum gasoline content of at least 15% by volume), diesel fuels, or as fuels for fuel cells. Methanol and dimethyl ether also are convenient energy storage and transportation materials that minimize or eliminate the disadvantages and dangers inherent in the use and transportation of LNG or LPG. Dimethyl ether is also a convenient household gas that can replace natural gas or can be mixed with natural or liquefied petroleum gas. Dimethyl ether is a high cetane value diesel substitute.

Methanol and dimethyl ether also are convenient raw materials for producing olefins, derived hydrocarbon products and polymers. Various products that can be made with methanol, dimethyl ether, or other methanol-derived chemicals are well known and include basic chemicals such as formaldehyde, acetic acid, methyl-tert-butyl ether (MTBE); olefins such as ethylene and propylene, which in turn can be used to form ethanol and propanol, higher olefins, polyolefins, synthetic hydrocarbons, and aromatic compounds; various other polymers; and chemicals such as chloromethanes, methylamines, methyl methacrylate, and dimethyl terephthalate, which can be further processed to manufacture products such as paints, resins, silicones, adhesives, antifreeze, plastics, and construction materials. These and other uses of methanol, dimethyl ether, and their derivative products are well known and will be appreciated by ordinary-skilled artisans. These products retain the carbon rather than releasing it into the atmosphere. At the end of the useful life of these materials, and in particular for polymers, they can be recycled and made into new polymeric products. Furthermore, materials that are not usable for recycling can be combusted with the carbon dioxide recovered as discussed above and then recycled to make methanol.

Another use for methanol is as a source for preparing single-cell proteins for human or animal consumption. Again, the carbon dioxide that is recovered and made into methanol is put to use rather than being emitted as an off-gas.

The invention as disclosed can permanently avoid or mitigate the release of the carbon dioxide into the environment during processing or combustion of petroleum oil by recycling it to methanol fuel and derived products. Carbon dioxide generated by any use of petroleum oil is captured and recycled so that it is not emitted to the atmosphere, thus rendering the petroleum oil a carbon dioxide-neutral fuel and source material. The recycling method can be repeated as many times as desired. As noted, methanol by itself or mixed with gasoline, ethanol or similar liquids can be used as a fuel that can be combusted in power plants to generate electricity. After being combusted, the carbon dioxide can be captured and recovered for re-use in making methanol for future use. This collection and recycling of the generated carbon dioxide avoids its release into the atmosphere, or avoids the need for temporary sequestration underground or in the sea, which in a long run untenable.

The invention is not to be limited in scope to the specific embodiments herein disclosed, as these embodiments are intended as illustrative aspects of the invention. Any equivalent embodiments will become apparent to those of ordinary skill in the art and are intended to be included within the scope of the invention.

EXAMPLES

The following examples are provided for purposes of illustrating preferred embodiments of the invention and are not limiting.

Example 1

Carbon dioxide generated during refining or combustion of petroleum oil (e.g., in a power plant) is directed to a capture and purification process rather than being emitted to the atmosphere. Carbon dioxide is removed by being adsorbed or by passing through any suitable adsorbing system containing an adsorbent that is known to efficiently adsorb carbon dioxide. An efficient adsorbent system for removing carbon dioxide can include a polyethyleneimine polymer or other polyamino-group containing polymers supported on fumed silica, alumina or other suitable support of nano-structured nature with a high surface area or activity, according to U.S. Pat. Application Publication No. 2008/0293976. Carbon dioxide is subsequently desorbed by heating or applying reduced pressure, and is then chemically recycled instead of being sequestered. Carbon dioxide thus obtained can then be used as a reactant and regenerative carbon source in the processes disclosed herein.

Example 2

Carbon dioxide is captured and purified from the exhausts of petroleum oil refineries and power plants or any other industrial plants according to Example 1 by any known and suitable method, e.g., absorption by nano-structured fumed silica, alumina as disclosed. It is then subsequently converted to methanol, dimethyl ether or derived products according to the processes disclosed herein, instead of being sequestered.

Example 3

A suitable molar mixture of $CO_2$, light hydrocarbon fraction of oil refining containing $C_1$ to $C_4$ alkanes, and steam is bi-reformed in one single step, allowing for a conversion of $CO_2$ in excess of 90% in a flow reactor over a metal oxide catalyst such as $V_2O_5/NiO$ at a temperature of about 800° C. to 850° C. to produce a gas mixture with a molar ratio of approximately 2.05 moles of hydrogen to 1 mole of carbon monoxide. The catalyst support is preferably fused silica (or alumina) having suitably large nano-structured surfaces. The reaction can also be performed in two separate steps utilizing the well-known steam reforming and dry reforming steps.

Example 4

Hydrogen and carbon monoxide produced in a suitable ratio of 2:1 as in Example 3 are subsequently converted to produce methanol under catalytic reaction conditions using suitable copper based catalysts.

Example 5

The methanol produced in Example 4 is dehydrated using a solid acidic catalyst such as silica, alumina or synthetic polymeric sulfonic acids such as Nafion-H to produce dimethyl ether.

Example 6

The water produced in the process of producing dimethyl ether in Example 5 is recycled to allow for the continuous conversion of $CO_2$ with methane (natural gas) to produce dimethyl ether, such that water is completely reused in the process.

Example 7

The methanol produced in Examples 4 is converted to useful transportation fuels by mixing with gasoline and optionally with a small amount of ethanol. The fuel is transported to a power plant or other energy producing facility where it can be combusted in place of coal, oil or natural gas. In this plant, the carbon dioxide that is generated is captured and recovered for recycling to produce further methanol.

Example 8

The dimethyl ether produced in Examples 5 and 6 is used a diesel substitute and as liquefied petroleum gas or natural gas substitutes. The fuel is transported to a power plant or other energy producing facility where it can be combusted in place of coal, oil or natural gas.

What is claimed is:

1. A method for rendering petroleum oil as an essentially environmentally carbon dioxide-neutral fuel and regenerative carbon source for producing methanol or dimethyl ether, which comprises: subjecting petroleum oil to refining or combustion conditions sufficient to produce carbon dioxide; capturing and purifying the produced carbon dioxide; and combining the purified carbon dioxide with water and a suitable light hydrocarbon fraction having the formulation of $C_nH_{(2n+2)}$, wherein n=1-4, in a molar ratio of 3:(3n-1):1 as $3C_nH_{(2n+2)}+(3n-1)H_2O+CO_2$ to conduct a bi-reforming reaction by:

conducting steam reforming of the light hydrocarbon fraction with water to form carbon monoxide and hydrogen as follows:

$$(3-1/n)[C_nH_{(2n+2)}+2nH_2O \rightarrow nCO+(2n+1)H_2];$$

conducting dry reforming of the light hydrocarbon fraction with carbon dioxide to form carbon monoxide and hydrogen as follows:

$$1/n[C_nH_{(2n+2)}+nCO_2 \rightarrow 2nCO+(n+1)H_2];$$

combining effluents including carbon monoxide and hydrogen from the steam and dry reforming reactions without separation of components of the reforming reactions or their effluents to produce a mixture of hydrogen and carbon monoxide having a molar ratio of hydrogen to carbon monoxide that is about 2:1 to 2.1:1; and converting the molar mixture of hydrogen and carbon monoxide under conditions sufficient to exclusively form methanol, as follows:

$$(3n+1)CO+(6n+2)H_2 \rightarrow (3n+1)CH_3OH,$$

so that the carbon dioxide generated from the petroleum oil is not introduced into the atmosphere, thus rendering the petroleum oil as an essentially environmentally carbon dioxide-neutral fuel and regenerative carbon source.

2. The method of claim 1 which further comprises: recycling the methanol or dimethyl ether for use as a fuel or feedstock; subjecting the methanol or dimethyl ether fuels or products made from the feedstock to further use to generate carbon dioxide; and repeating the capturing, combining, recycling and conversion steps of the generated carbon dioxide so that the carbon dioxide produced from the methanol fuels or products made from the methanol feedstock also is not released into the atmosphere.

3. The method of claim 1, wherein the combustion of petroleum oil in a power plant generates energy.

4. The method of claim 1, wherein the carbon dioxide, suitable light hydrocarbon fraction, and water are combined in suitable molar ratios and are reacted in separate steps or in a single step to produce methanol.

5. The method of claim 1, wherein the suitable hydrocarbon fractions are saturated hydrocarbons including methane, ethane, propane and butanes.

6. The method of claim 1, which further comprises: combusting the petroleum oil while producing carbon dioxide; capturing the produced carbon dioxide on an adsorbent; and treating the adsorbent to release the captured carbon dioxide therefrom for use in producing methanol or dimethyl ether.

7. The method of claim 6, wherein the adsorbent is treated with sufficient heating, reduced pressure, vacuum, gas purge, or a combination thereof to release the captured carbon dioxide.

8. The method of claim 6, wherein the absorbent is a polyamino-containing polymer deposited on a nano-structured supporting having a high surface area.

9. The method of claim 8, wherein the polyamino-containing polymer is polyethyleneimine and the support is nano-structured fused silica or alumina.

10. The method of claim 1, wherein the steam reforming and the dry reforming are performed simultaneously in a single bi-reforming step.

11. The method of claim 10, wherein the light hydrocarbon fraction, steam and carbon dioxide are reacted in a single step in a suitable molar ratio to form a mixture of hydrogen and carbon dioxide in a molar ratio of about 2:1.

12. The method of claim 1, wherein the bi-reforming is carried out over a catalyst at a temperature between about 800° C. and 1100° C.

13. The method of claim 12, wherein the catalyst is provided on a support of a high surface area nano-structured fumed alumina or fumed silica.

14. The method of claim 12, wherein the catalyst comprises V, Ti, Ga, Mg, Cu, Ni, Mo, Bi, Fe, Mn, Co, Nb, Zr, La or Sn, or an oxide thereof.

15. The method of claim 12, wherein the catalyst comprises a single metal catalyst, a single metal oxide catalyst, a mixed catalyst of a metal and a metal oxide, or a mixed catalyst of at least one metal oxide and another metal oxide, the catalyst optionally being provided on an oxide support.

16. The method of claim 15, wherein the catalyst is NiO or a mixed catalyst of NiO, $V_2O_5$:$Ni_2O_3$, $Ni_2V_2O_7$ and $Ni_3V_2O_5$.

17. The method of claim 15, wherein the catalyst is NiO supported on fumed alumina or NiO/$V_2O_5$ supported on fumed silica.

18. The method of claim 1, which further comprises dehydrating methanol by removing water under conditions sufficient to produce dimethyl ether and recycling the water from dehydration during subsequent reforming.

19. The method of claim 18, which further comprises reacting the dimethyl ether in the presence of an acidic-basic or zeolitic catalyst under conditions sufficient to form ethylene or propylene.

20. The method of claim 19, which further comprises converting ethylene or propylene under conditions sufficient to produce synthetic hydrocarbons, chemicals, or polymers.

21. The method of claim 1, which further comprises combusting the produced methanol, optionally in a mixture that includes gasoline, in a power plant that produces energy with the combusted methanol while also generating carbon dioxide and recycling the generated carbon dioxide for producing methanol.

22. The method of claim 18, which further comprises combusting the produced dimethyl ether, as diesel oil substitute, optionally in a mixture that includes natural and light petroleum gas, in a power plant that produces energy while also generating carbon dioxide and recycling the generated carbon dioxide for producing methanol which in turn produces additional dimethyl ether.

* * * * *